(12) United States Patent
Kim

(10) Patent No.: US 10,631,817 B2
(45) Date of Patent: Apr. 28, 2020

(54) MOBILE X-RAY APPARATUS AND METHOD OF OPERATING THE SAME

(71) Applicant: SAMSUNG ELECTRONICS CO., LTD., Suwon-si (KR)

(72) Inventor: Myeong-je Kim, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 269 days.

(21) Appl. No.: 15/798,918

(22) Filed: Oct. 31, 2017

(65) Prior Publication Data

US 2018/0116625 A1    May 3, 2018

(30) Foreign Application Priority Data

Oct. 31, 2016   (KR) .......................... 10-2016-0143428

(51) Int. Cl.
*A61B 6/00* (2006.01)
*G01R 31/3842* (2019.01)
*G01R 31/389* (2019.01)

(52) U.S. Cl.
CPC .............. *A61B 6/56* (2013.01); *A61B 6/4405* (2013.01); *G01R 31/389* (2019.01); *G01R 31/3842* (2019.01); *A61B 6/4283* (2013.01); *A61B 6/461* (2013.01)

(58) Field of Classification Search
None
See application file for complete search history.

(56) References Cited

U.S. PATENT DOCUMENTS

| 3,878,394 | A | * | 4/1975 | Golden | H01F 27/40 |
| | | | | | 378/102 |
| 6,586,940 | B2 | | 7/2003 | Asakura et al. | |
| 8,415,926 | B2 | * | 4/2013 | Bhardwaj | G01R 31/389 |
| | | | | | 320/134 |
| 9,406,982 | B2 | | 8/2016 | Obata | |
| 2004/0239332 | A1 | | 12/2004 | Mackel et al. | |
| 2008/0169819 | A1 | | 7/2008 | Ishii | |
| 2010/0332166 | A1 | * | 12/2010 | Shin | G01R 31/392 |
| | | | | | 702/63 |
| 2012/0004875 | A1 | | 1/2012 | Maeda et al. | |

FOREIGN PATENT DOCUMENTS

| JP | 56-69899 U | 6/1981 |
| JP | 61-126800 A | 6/1986 |
| JP | 2001-332310 A | 11/2001 |
| JP | 2010-261807 A | 11/2010 |
| JP | 2013-131338 A | 7/2013 |
| KR | 10-1160545 B1 | 6/2012 |

OTHER PUBLICATIONS

Communication dated Mar. 29, 2018, issued by the European Patent Office in counterpart European Patent Application No. 17198857.9.

* cited by examiner

*Primary Examiner* — Edwin C Gunberg
(74) *Attorney, Agent, or Firm* — Sughrue Mion, PLLC

(57) ABSTRACT

Provided are a mobile X-ray apparatus and a method of operating the same. The mobile X-ray apparatus may include an X-ray emitter; a battery configured to supply operating power to the X-ray emitter; and a controller configured to calculate an internal resistance value of a battery based on an overcurrent generated when X-rays are emitted by an X-ray emitter, and determine a degradation state of the battery by using the calculated internal resistance value.

17 Claims, 9 Drawing Sheets

| | INITIAL CHARGING TIME | CHARGING TIME AFTER FULL DEGRADATION | CURRENT CHARGING TIME |
|---|---|---|---|
| DRIVING MODE | 4 HOURS | 2 HOURS | ☐ HOURS |
| SLEEP MODE | 3 HOURS | 1.5 HOURS | ☐ HOURS |
| POWER-OFF MODE | 2 HOURS | 1 HOURS | 1.5 HOURS |

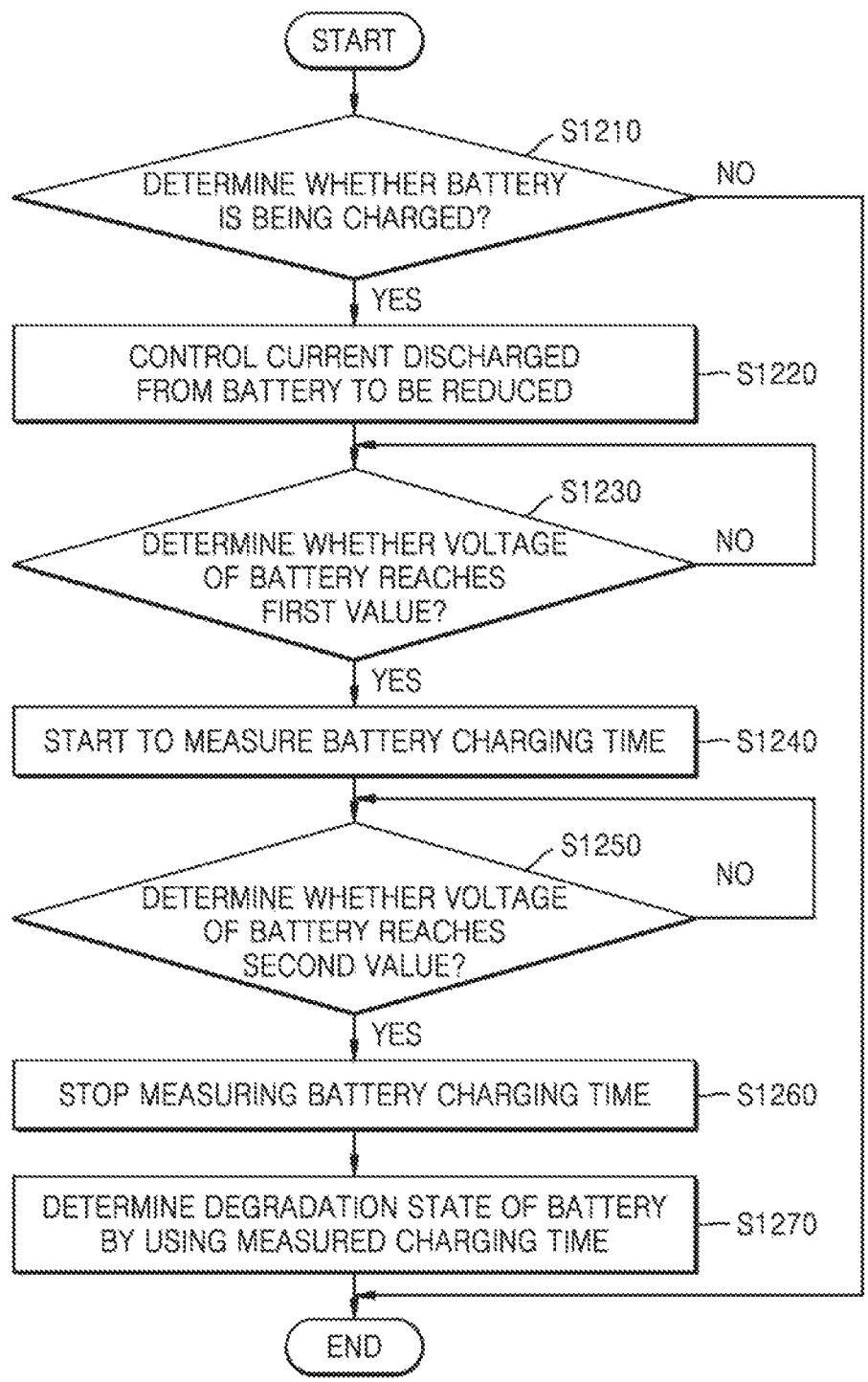

MOBILE X-RAY APPARATUS AND METHOD OF OPERATING THE SAME

CROSS-REFERENCE TO RELATED APPLICATION

This application claims priority from Korean Patent Application No. 10-2016-0143428, filed on Oct. 31, 2016, in the Korean Intellectual Property Office, the disclosure of which is incorporated herein in its entirety by reference.

BACKGROUND

1. Field

Apparatuses and methods consistent with example embodiments relate to a mobile X-ray apparatus for determining a degradation state of a battery and a method of operating the mobile X-ray apparatus.

2. Description of the Related Art

X-rays, which are electromagnetic waves having a wavelength ranging from 0.01 Å to 100 Å, may pass through an object and thus are widely used in medical devices for imaging the interior of a living body or in nondestructive testing devices of other industries.

An X-ray apparatus using X-rays may obtain an X-ray image of an object by transmitting X-rays emitted from an X-ray source through the object and detecting an intensity difference of the transmitted X-rays by using an X-ray detector. The X-ray apparatus may inspect an internal structure of the object and diagnose the object by using the X-ray image. X-ray apparatuses have advantages in that an internal structure of an object may be easily inspected based on the principle that the transmittance of X-rays varies according to an atomic number of atoms of the object and a density of the object. When a wavelength of X-rays decreases, a transmittance increases and a brightness of the image shown on a screen increases.

SUMMARY

One or more example embodiments provide a mobile X-ray apparatus for determining a degradation state of a battery and a method of operating the mobile X-ray apparatus.

Additional aspects will be set forth in part in the description which follows and, in part, will be apparent from the description, or may be learned by practice of the presented embodiments.

According to an aspect of an example embodiment, a mobile X-ray apparatus may include: an X-ray emitter; a battery configured to supply operating power to the X-ray emitter; and a controller configured to calculate an internal resistance value of the battery based on an overcurrent generated when X-rays are emitted by the X-ray emitter, and determine a degradation state of the battery by using the calculated internal resistance value.

According to an aspect of an example embodiment, a method of operating a mobile X-ray apparatus including a battery may include: calculating an internal resistance value of the battery by using an overcurrent generated when X-rays are emitted by the mobile X-ray apparatus; and determining a degradation state of the battery by using the calculated internal resistance value.

According to an aspect of an example embodiment, a mobile X-ray apparatus may include: a battery configured to supply operating power to the mobile X-ray apparatus; a charger configured to charge the battery; and a controller configured to, while a current being discharged from the battery is maintained at a reduced discharge rate, measure a charging time taken for the charger to charge the battery and determine a degradation state of the battery based on the measured charging time.

According to an aspect of an example embodiment, a computer-readable recording medium may have embodied thereon a program for executing the method in a computer.

BRIEF DESCRIPTION OF THE DRAWINGS

These and/or other aspects will become apparent and more readily appreciated from the following description of the example embodiments, taken in conjunction with the accompanying drawings in which:

FIG. 12 is a flowchart of a method of operating the X-ray apparatus, according to an example embodiment.

DETAILED DESCRIPTION

Figure 1:
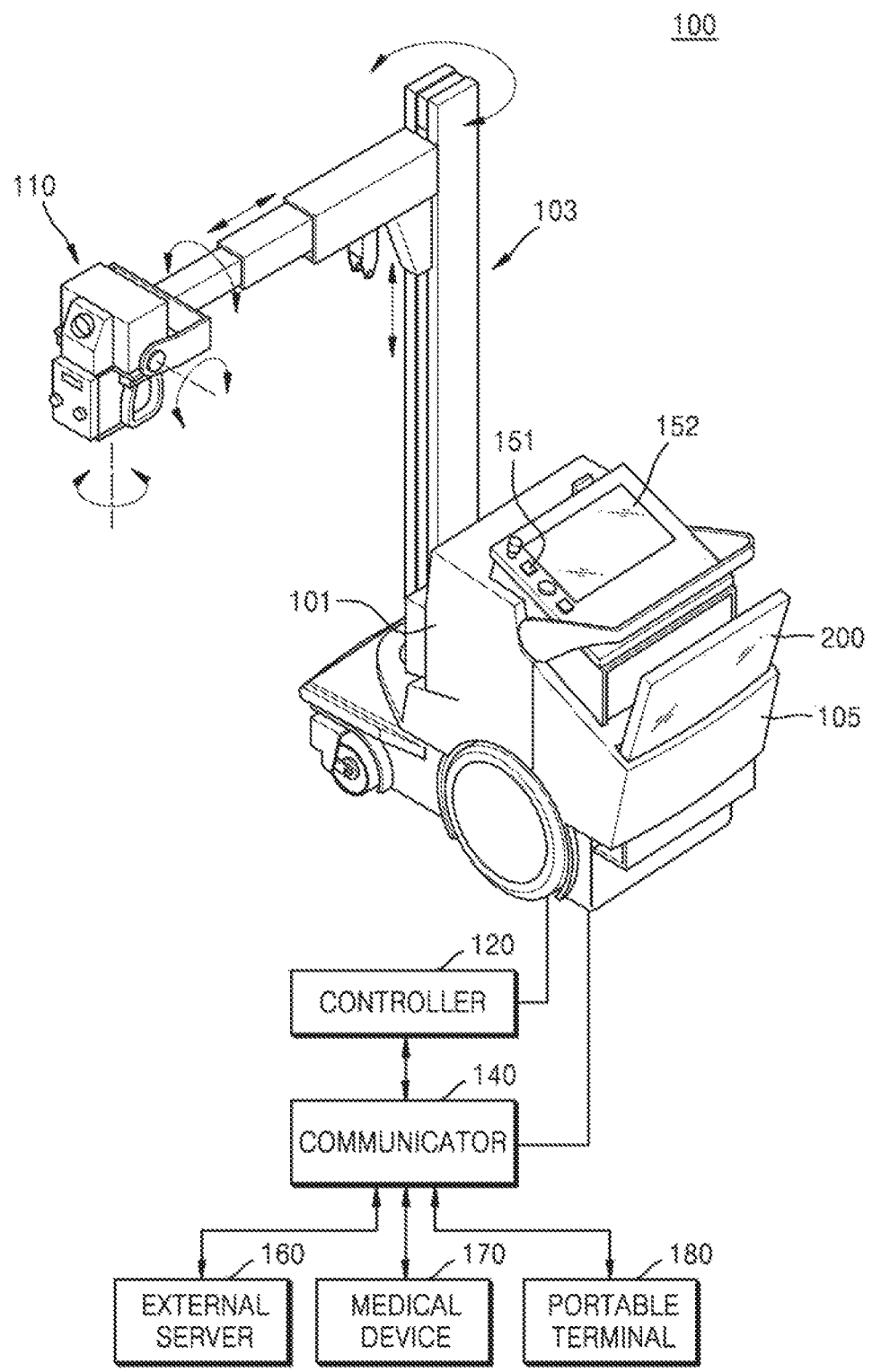
FIG. 1 is a perspective view illustrating an outer appearance of an X-ray apparatus that is a mobile X-ray apparatus.

Hereinafter, principles and example embodiments of the present disclosure will be described in detail in order to fully convey the scope of the present disclosure and enable one of ordinary skill in the art to embody and practice the present disclosure. The example embodiments may be implemented in various forms.

The same reference numerals denote the same elements throughout the specification. All elements of example embodiments are not described in the specification, and descriptions of matters well known in the art to which the present disclosure pertains or repeated descriptions between example embodiments will not be given. Terms such as "part" and "portion" used herein denote those that may be embodied by software or hardware. According to example embodiments, a plurality of parts or portions may be embodied by a single unit or element, or a single part or portion may include a plurality of elements. Operation principles and example embodiments of the present disclosure will now be explained with reference to the accompanying drawings.

In the present specification, an image may include a medical image obtained by a magnetic resonance imaging (MRI) apparatus, a computed tomography (CT) apparatus, an ultrasound imaging apparatus, an X-ray apparatus, or another medical imaging apparatus.

Furthermore, in the present specification, an "object" may be a target to be imaged and may include a human, an animal, or a part of a human or animal. For example, the object may include a body part (an organ, a tissue, etc.) or a phantom.

FIG. 1 is a perspective view illustrating an outer appearance of an X-ray apparatus 100 that is a mobile X-ray apparatus.

Referring to FIG. 1, the X-ray apparatus 100 includes an X-ray emitter 110 configured to generate and emit X-rays, an input interface 151 configured to receive a command from a user, a display 152 configured to provide information to the user, a controller 120 configured to control the X-ray apparatus 100 according to the command, and a communicator 140 configured to communicate with an external device.

The X-ray emitter 110 may include an X-ray source for generating X-rays, and a collimator for adjusting a radiation field of X-rays generated by the X-ray source.

When the X-ray apparatus 100 is a mobile X-ray apparatus, since a main body 101 to which the X-ray emitter 110 is connected may freely move and an arm 103 for connecting the X-ray emitter 110 to the main body 101 may also rotate and linearly move, the X-ray emitter 110 may freely move in a three-dimensional (3D) space.

The input interface 151 may receive a command for controlling a position of the X-ray emitter 110, an imaging timing, an imaging condition, or an imaging protocol. The input interface 151 may include a keyboard, a mouse, a touchscreen, and/or a speech recognizer.

The display 152 may display a screen for guiding a user input, an X-ray image, and/or a screen showing a state of the X-ray apparatus 100.

The controller 120 may control an imaging timing and an imaging condition of the X-ray emitter 110 according to a control command input from the user, and may generate a medical image by using image data received from an X-ray detector 200. Also, the controller 120 may control a position or an attitude (i.e., orientation) of the X-ray emitter 110 according to a position of an object P and an imaging protocol.

The controller 120 may include a memory in which a program for performing operations described above and below is stored and a processor for executing the stored program. The controller 120 may include a single processor or a plurality of processors. When the controller 120 includes a plurality of processors, the plurality of processors may be integrated into one chip or may be physically separated from one another.

A storage 105 for storing the X-ray detector 200 may be provided on the main body 101. Also, a charging terminal for charging the X-ray detector 200 may be provided in the storage 105. Accordingly, the X-ray detector 200 may be charged while being stored in the storage 105.

The input interface 151, the display 152, the controller 120, and the communicator 140 may be provided in the main body 101. Image data obtained by the X-ray detector 200 may be transmitted to the main body 101 to be processed, and then may be displayed on the display 152 or transmitted to an external device through the communicator 140.

Also, the controller 120 and the communicator 140 may be physically separated from the main body 101, or some elements of the controller 120 and the communicator 140 may be provided in the main body 101.

The X-ray apparatus 100 may be connected to an external device, such as an external server 160, a medical device 170, and/or a portable terminal 180 (e.g., a smartphone, a tablet personal computer (PC), or a wearable device), through the communicator 140 and may transmit or receive data to or from the external device.

The communicator 140 may include one or more elements that may perform communication with the external device, and may include at least one from among, for example, a short-range communication module, a wired communication module, and a wireless communication module.

Alternatively, the communicator 140 may receive a control signal from the external device and may transmit the received control signal to the controller 120, and the controller 120 may control the X-ray apparatus 100 according to the received control signal.

Also, the controller 120 may transmit a control signal to the external device through the communicator 140 and may control the external device according to the control signal of the controller 120. For example, the external device may process data of the external device according to the control signal of the controller 120 received through the communicator 140.

Also, the communicator 140 may further include an internal communication module for performing communication between elements of the X-ray apparatus 100. A program for controlling the X-ray apparatus 100 may be installed in the external device, and may include a command for performing some or all of operations of the controller 120.

The program may be previously installed in the portable terminal 180, or may be downloaded by a user of the portable terminal 180 from a server that provides an application and then may be installed. The server that provides the application may include a computer-readable recording medium in which the program is stored.

Also, the communicator 140 may further include an internal communication module for performing communication between elements of the X-ray apparatus 100.

Figure 2:
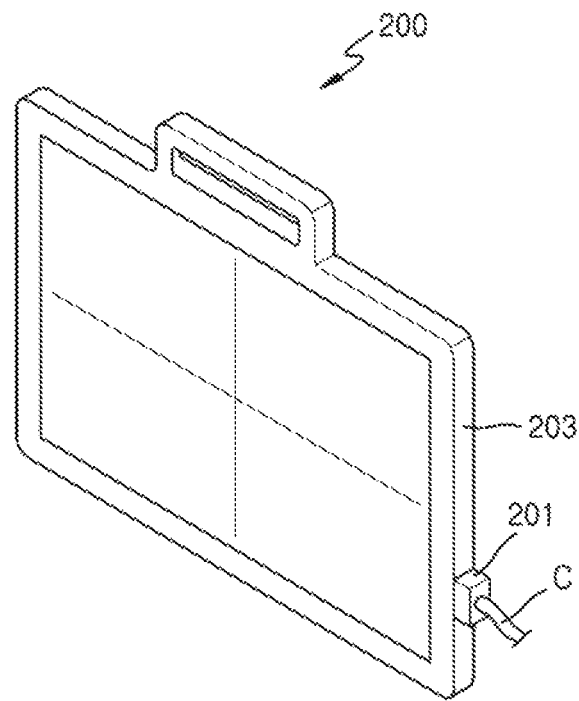
FIG. 2 is a perspective view illustrating an outer appearance of an X-ray detector.

FIG. 2 is a perspective view illustrating an outer appearance of the X-ray detector 200.

As described above, the X-ray detector 200 used in the X-ray apparatus 100 may be implemented as a portable X-ray detector. The X-ray detector 200 may be equipped with a battery for supplying power to operate wirelessly (e.g., cordlessly), or as shown in FIG. 2, may operate by connecting a charge port 201 to a separate power supply via a cable C.

A case 203 forms an outward appearance of the X-ray detector 200 and has therein a plurality of detecting elements for detecting X-rays and converting the X-rays into image data, a memory for temporarily or permanently storing the image data, a communication module for receiving a control signal from the X-ray apparatus 100 or transmitting the image data to the X-ray apparatus 100, and a battery. Further, image correction information and intrinsic identification (ID) information of the X-ray detector 200 may be stored in the memory, and the stored ID information may be transmitted together with the image data during communication with the X-ray apparatus 100.

Figure 3:
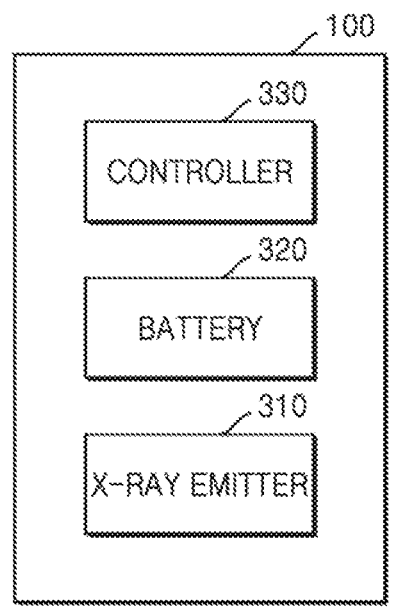
FIG. 3 is a block diagram of the X-ray apparatus according to an example embodiment.

FIG. 3 is a block diagram of the X-ray apparatus 100 according to an example embodiment.

The X-ray apparatus 100 may include an X-ray emitter 310, a battery 320, and a controller 330. The X-ray apparatus 100 of FIG. 3 may be a mobile X-ray apparatus like in FIG. 1, and only elements related to the present example embodiment are illustrated. Accordingly, it will be understood by one of ordinary skill in the art that elements other than the elements illustrated in FIG. 3 may be further included.

The X-ray emitter 310 may correspond to the X-ray emitter 110 of FIG. 1, and thus a repeated explanation will not be given. Also, the controller 330 may correspond to the controller 120 of FIG. 1, and thus a repeated explanation will not be given.

The battery 320 may supply operating power to the X-ray emitter 310 and the controller 330. Also, the battery 320 may supply operating power to elements of the X-ray apparatus 100 that require operating power. For example, the battery 320 may supply operating power to the input interface 151, the display 152, and the communicator 140 of the X-ray apparatus 100.

According to an aspect of an example embodiment, the battery 320 may be a rechargeable battery. For example, the battery 320 may be a lithium-ion battery having a structure in which a plurality of battery cells are connected and coupled to one another.

The controller 330 may calculate an internal resistance value of the battery 320 by using overcurrent generated when the X-ray emitter 310 emits X-rays, and may determine a degradation state of the battery 320 by using the calculated internal resistance value. The degradation state of the battery 320 may indicate, for example, reduced capacity, cycle life, safety, etc. due to chemical changes that occur to the battery's electrodes over time.

Overcurrent may temporarily flow through the battery 320 when X-rays are emitted, and a voltage of the battery 320 may be reduced due to the overcurrent. Accordingly, the controller 330 may calculate an internal resistance value of the battery 320 based on a change in current and a voltage of the battery 320 when X-rays are emitted. According to an aspect of an example embodiment, the controller 330 may obtain an initial voltage value of the battery 320 before X-rays are emitted, obtain a maximum current value and a minimum voltage value of the battery 320 when X-rays are emitted, and calculate an internal resistance value of the battery 320 by using the obtained initial voltage value, maximum current value, and minimum voltage value. For example, the controller 330 may calculate an internal resistance value of the battery 320 by using Equation 1.

$$\text{Internal resistance value} = \frac{\text{Initial voltage value} - \text{Minimum voltage value}}{\text{Maximum current value}} \qquad (1)$$

The controller 330 may determine a degradation state of the battery 320 by comparing an initial internal resistance value of the battery 320 with a calculated current internal resistance value of the battery 320. Since an internal resistance value increases as the battery 320 is degraded, the controller 330 may determine how much the battery 320 is degraded when compared to its initial state by checking how much an internal resistance value of the battery 320 has increased from an initial internal resistance value. For example, when the battery is completely degraded, an internal resistance value of the battery 320 may be about twice an initial internal resistance value, and the controller 330 may determine how much the battery 320 is degraded by checking by how much a current internal resistance value of the battery has increased over the initial internal resistance value.

In an example embodiment, the controller 330 may determine a remaining lifetime of the battery 320 based on the calculated internal resistance value of the battery 320. The controller 330 may determine a remaining lifetime by determining how much the battery 320 has degraded when compared to its initial state by checking how much an internal resistance value of the battery 320 has increased from an initial internal resistance value. For example, assuming that an internal resistance value of the battery 320 is twice as high as an initial internal resistance value when the battery 320 is completely degraded and a total life expectancy of the battery is 4 years, then when the controller 330 detects that a current internal resistance value of the battery 320 is 1.5 times as high as the initial internal resistance value, the controller 330 may determine that a remaining lifetime of the battery 320 is approximately 2 years.

Accordingly, since the X-ray apparatus 100 may determine a degradation state of the battery 320 by using an internal resistance value of the battery 320 calculated by using overcurrent generated when X-rays are emitted, the X-ray apparatus 100 may more reliably estimate the degradation sate of the battery 320. In the related art, since an internal resistance value of a battery is calculated by using low current continuously flowing through the battery, a deviation of the internal resistance value may be larger. However, in the present disclosure, since high current that is overcurrent generated when X-rays are emitted is used, a deviation of an internal resistance value may be reduced and thus a degradation state of the battery 320 may be more reliably estimated. Also, in the related art, low current continuously flowing through a battery may deviate according to a use pattern of an X-ray apparatus. However, in the present disclosure, since a high current, generated when a specific condition is satisfied such as when X-rays are emitted, is used, an internal resistance value of the battery 320 may be more reliably calculated.

Figure 4:
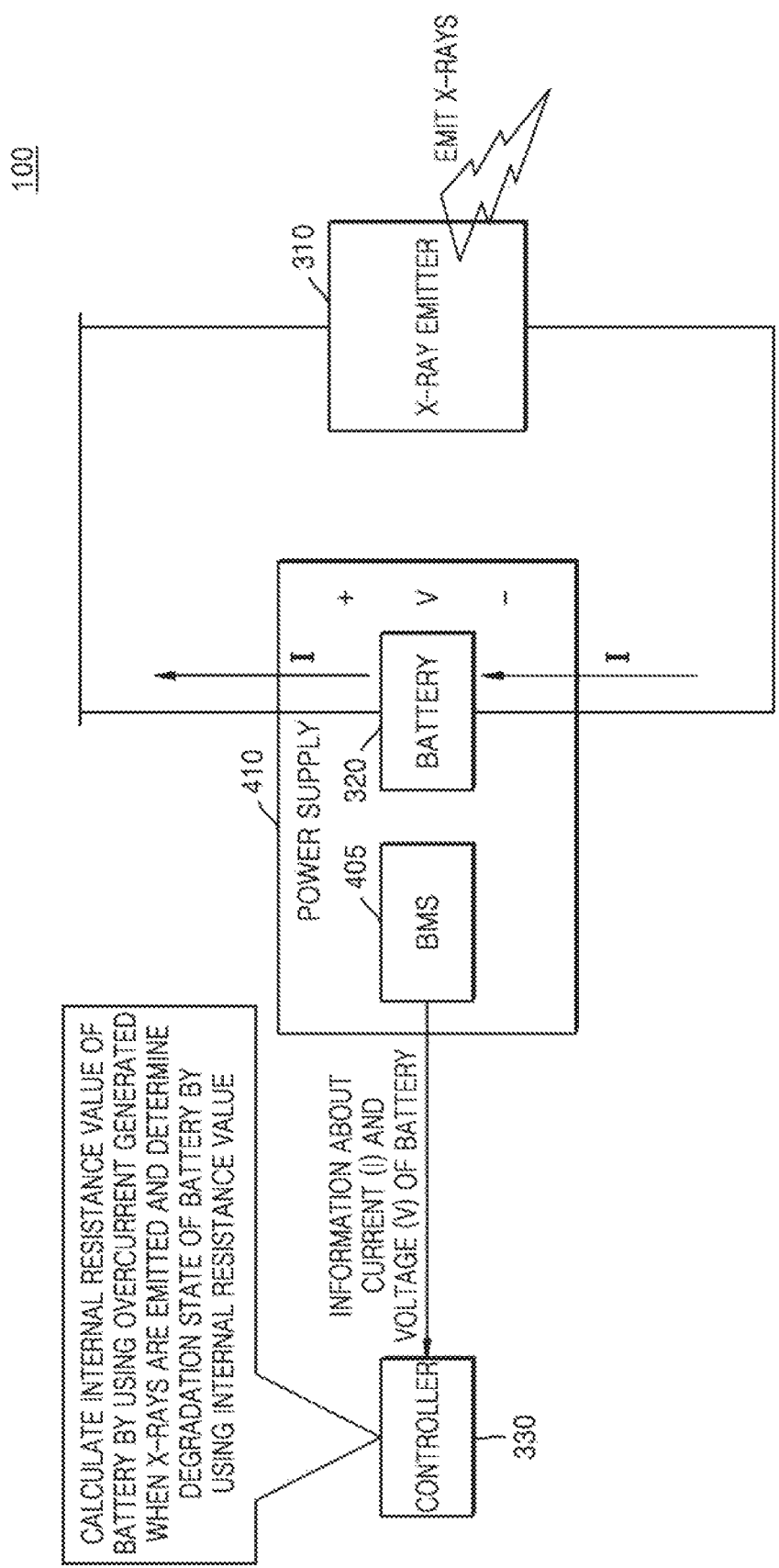
FIG. 4 is a block diagram of the X-ray apparatus according to an example embodiment.

FIG. 4 is a block diagram of the X-ray apparatus 100 according to an example embodiment.

The X-ray apparatus 100 may include the X-ray emitter 310, a power supply 410, and the controller 330. The power supply 410 may include the battery 320 and a battery management system (BMS) 405.

The BMS 405 may detect a state of the battery 320, for example, a voltage, a current, or a temperature of the battery 320. According to an aspect of an example embodiment, the BMS 405 may detect a voltage V of the battery 320 by using a circuit that is a battery stack monitor. Also, the BMS 405 may detect current I of the battery 320 by using a current sensor.

The controller 330 may periodically obtain information about the voltage V and the current I from the BMS 405. The power supply 410 and the controller 330 may each include a communication interface to communicate with each other. For example, the controller 330 may receive information about the voltage V and the current I of the battery 320 from the BMS 405 through controller area network (CAN) communication. Also, each of the power supply 410 and the controller 330 may be configured as a separate modular unit.

The controller 330 may obtain an initial voltage value of the battery 320 before X-rays are emitted, based on an X-ray emission ready signal. In more detail, the controller 330 may obtain the X-ray emission ready signal through the input interface 151. For example, when the input interface 151 is a hand switch, a user may press a button of the input interface 151 for issuing an X-ray emission command, and the controller 330 may obtain the X-ray emission ready signal through the pressed button of the input interface 151. Accordingly, the controller 330 may obtain a voltage value of the battery 320 corresponding to a point of time when the X-ray emission ready signal is generated as an initial voltage value.

Next, the controller 330 may determine a maximum current value and a minimum voltage value of the battery 320 when the X-rays are emitted (e.g., while the X-rays are emitted or after the X-rays are emitted), from among current values and voltage values of the battery 320 obtained during a predetermined period from the point of time when the X-ray emission ready signal is generated to a predetermined time. In more detail, the controller 330 may determine a maximum value from among the current values of the battery 320 obtained during the predetermined period as a maximum current value, and may determine a minimum value from among the voltage values of the battery 320 obtained during the predetermined period as a minimum voltage value. Accordingly, the controller 330 may calculate an internal resistance value of the battery 320 by using the obtained initial voltage value, maximum current value, and minimum voltage value. For example, the controller 330 may calculate an internal resistance value of the battery 320 by using Equation 1. A more detailed embodiment will be explained below with reference to FIG. 5.

The controller 330 may determine a degradation state of the battery 320 by using the calculated internal resistance value of the battery 320. Also, the controller 330 may determine a remaining lifetime of the battery 320 by using the calculated internal resistance value. Next, the X-ray apparatus 100 may display the remaining lifetime of the battery 320 on the display 152.

Figure 5:
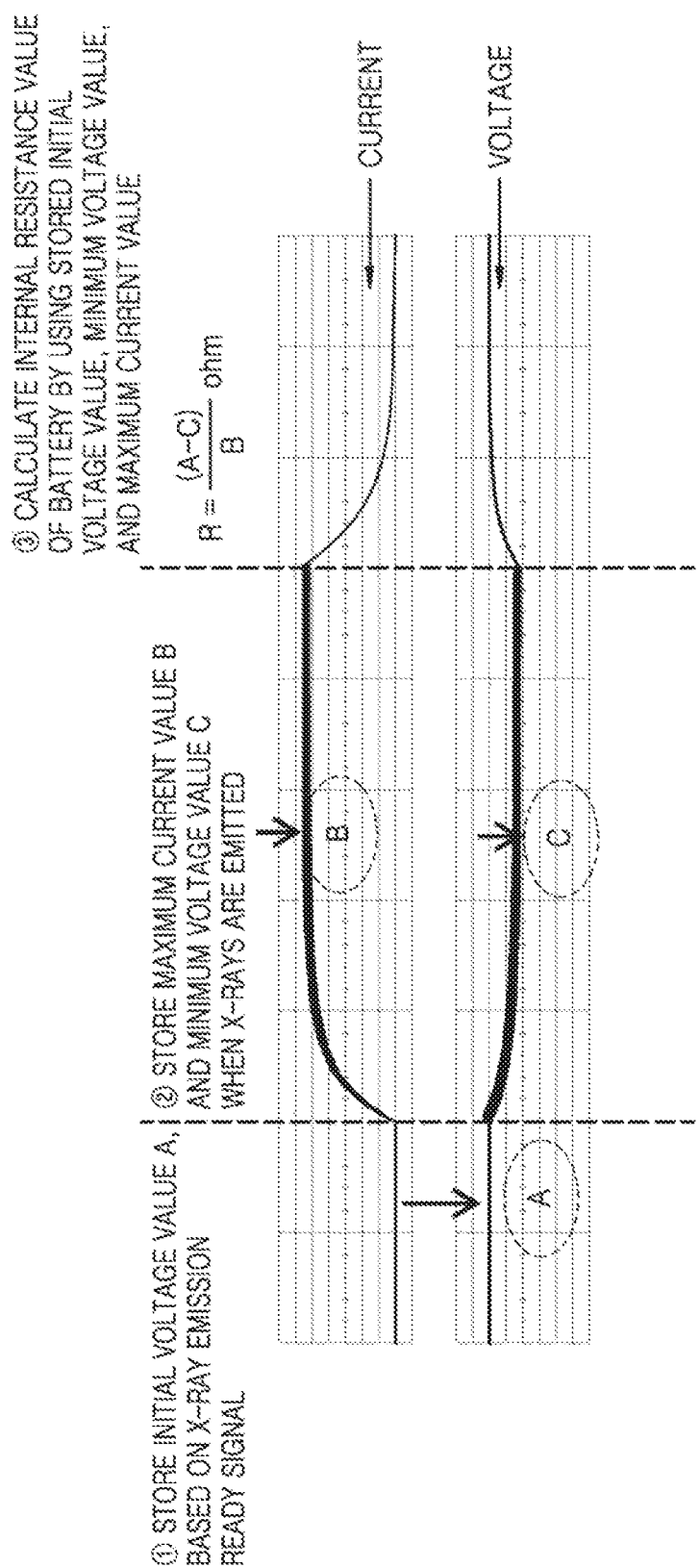
FIG. 5 is a graph illustrating an example where a controller calculates an internal resistance of a battery according to an example embodiment.

FIG. 5 is a graph illustrating an example where the controller 330 calculates an internal resistance value of the battery 320 according to an example embodiment.

The controller 330 may obtain a voltage value and a current value of the battery 320. According to an aspect of an example embodiment, the controller 330 may periodically receive information about the voltage value and the current value of the battery 320 from the power supply 410.

When an X-ray emission ready signal is generated, the controller 330 may obtain and store a voltage value A of the battery 320 corresponding to a point of time when the X-ray emission ready signal is generated as an initial voltage value.

The controller 330 may obtain and store a maximum current value B and a minimum voltage value C of the battery 320 while X-rays are emitted by monitoring current values and voltage values of the battery 320 obtained during a predetermined period from the point of time when the X-ray emission ready signal is generated to a predetermined time. As shown in the graph of FIG. 5, when the X-rays are emitted, since overcurrent may be generated and a voltage drop may occur, the controller 330 may obtain and store the maximum current value B and the minimum voltage value C of the battery 320 when the X-rays are emitted.

The controller 330 may calculate an internal resistance value (A-C)/B (ohm) of the battery 320 by using the stored initial voltage value A, maximum current value B, and minimum voltage value C.

Figure 6:
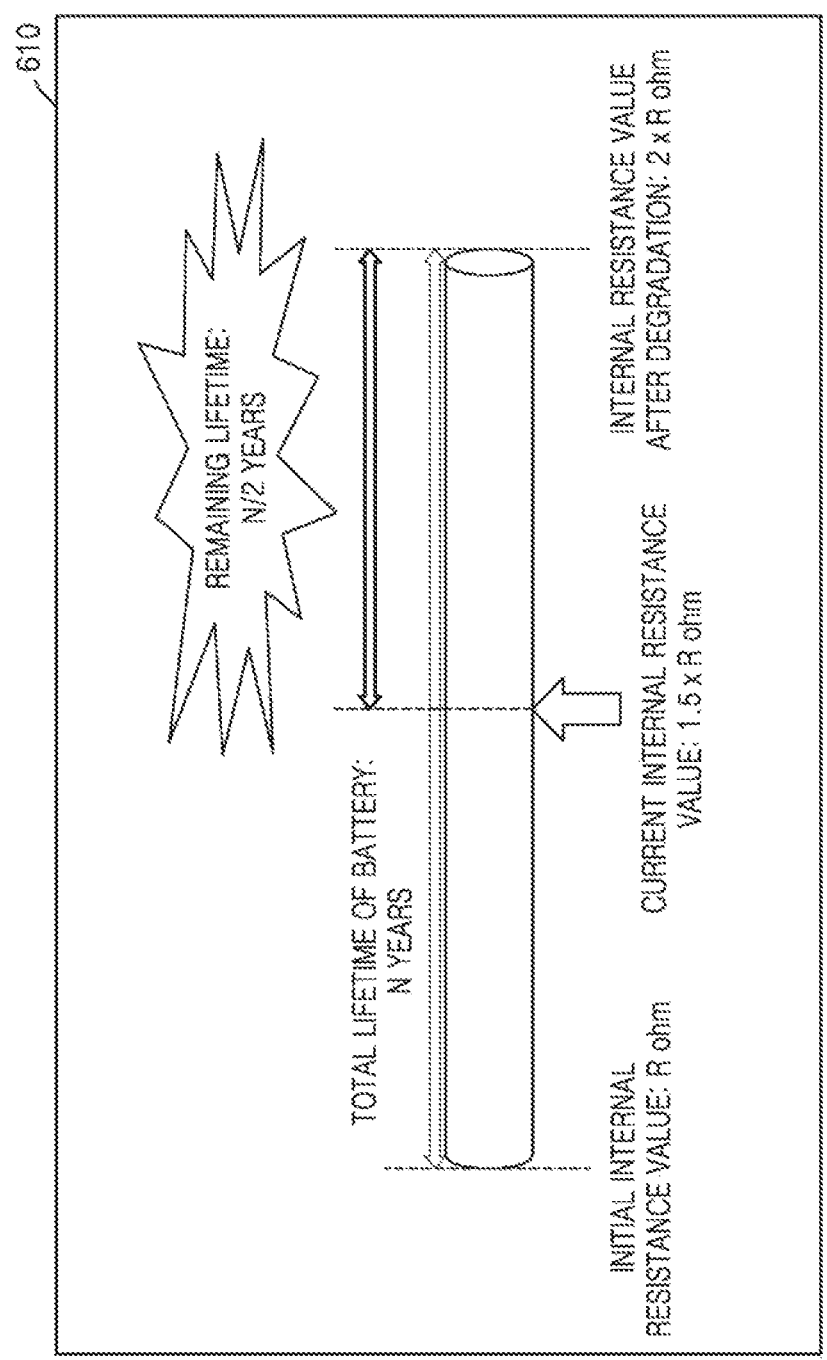
FIG. 6 is a view illustrating an example where the X-ray apparatus displays a remaining lifetime of the battery, according to an example embodiment.

FIG. 6 is a view illustrating an example where the X-ray apparatus 100 displays a remaining lifetime of the battery 320 according to an example embodiment.

According to an aspect of an example embodiment, the X-ray apparatus 100 may calculate a current internal resistance value 1.5×R of the battery 320 and may determine a degradation state and a remaining lifetime of the battery 320 by comparing an initial internal resistance value R with the current internal resistance value 1.5×R. Accordingly, as shown in a screen 610, the X-ray apparatus 100 may display the determined degradation state and remaining lifetime on the display 152.

In more detail, the X-ray apparatus 100 may determine that the battery 320 is degraded by 50% by checking that the current internal resistance value 1.5×R is an intermediate value between the initial resistance value R and an internal resistance value 2×R when the battery 320 is completely degraded. Also, since the battery 320 is degraded by 50%, the X-ray apparatus 100 may recognize that about half of a total lifetime of N years (where N is an integer) of the battery 320 remains. Accordingly, the X-ray apparatus 100 may determine that a remaining lifetime of the battery 320 is N/2 years, and may display the screen 610.

Figure 7:
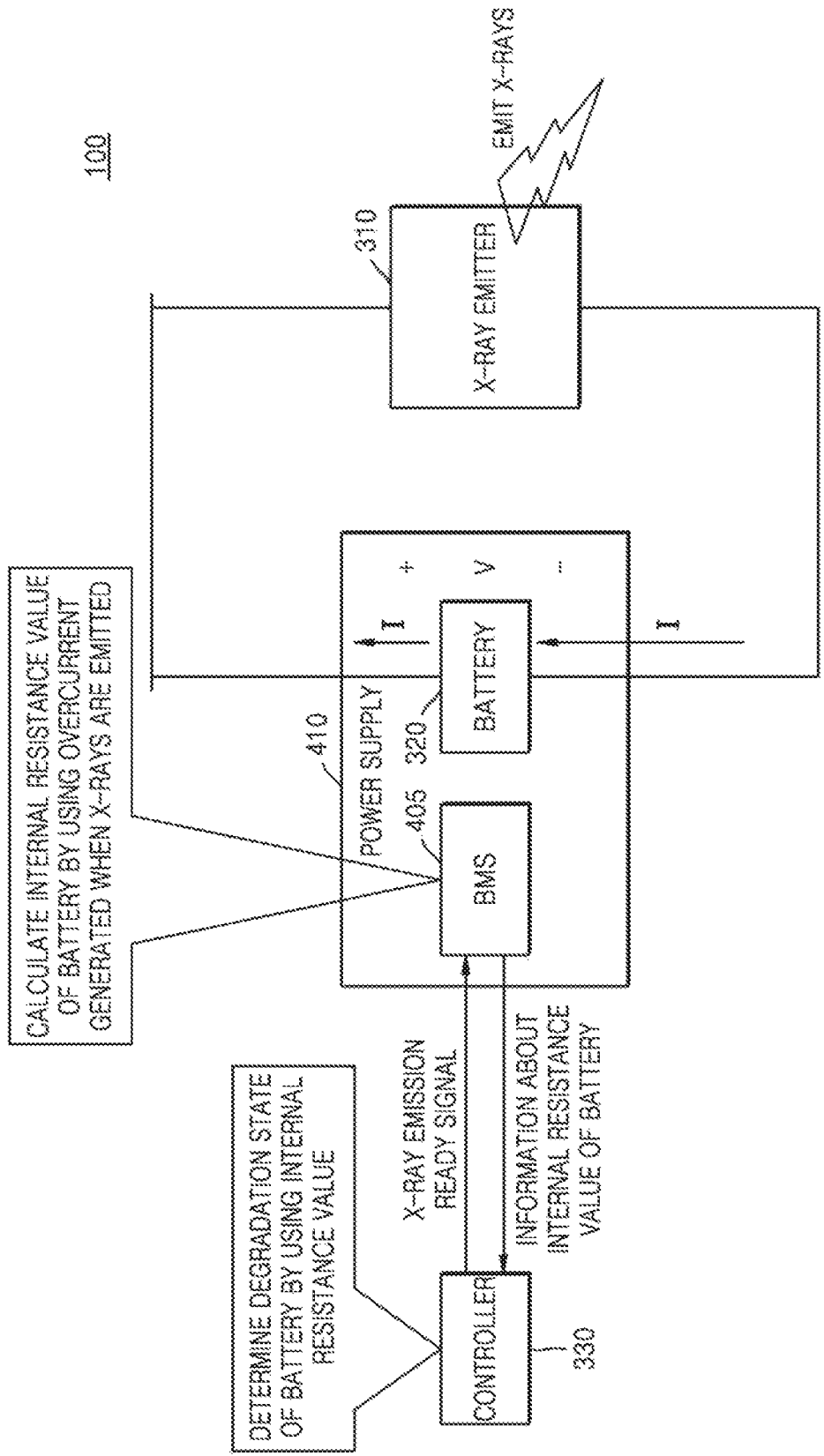
FIG. 7 is a block diagram of the X-ray apparatus according to an example embodiment.

FIG. 7 is a block diagram of the X-ray apparatus 100 according to an example embodiment.

The X-ray emitter 310, the power supply 410, and the controller 330 have been described with reference to FIG. 4, and thus a repeated explanation thereof will not be given.

The BMS 405 may detect a voltage and current of the battery 320, and may calculate an internal resistance value of the battery 320 by using the overcurrent generated when X-rays are emitted.

In more detail, the controller 330 may obtain an X-ray emission ready signal and may transmit the obtained X-ray emission ready signal to the BMS 405. Accordingly, the BMS 405 may obtain an initial voltage value of the battery 320 before the X-rays are emitted, based on the X-ray emission ready signal. Also, the BMS 405 may obtain a maximum current value and a minimum voltage value of the battery 320 when the X-rays are emitted. Next, the BMS 405 may calculate an internal resistance value of the battery 320 by using the obtained initial voltage value, maximum current value, and minimum voltage value. For example, the BMS 405 may calculate an internal resistance value of the battery 320 by using Equation 1.

The BMS 405 may transmit the calculated internal resistance value of the battery 320 to the controller 330. Accordingly, the controller 330 may determine a degradation state of the battery 320 by using the transmitted internal resistance value of the battery 320. Also, the controller 330 may determine a remaining lifetime of the battery 320 by using the transmitted internal resistance value of the battery 320. According to another example embodiment, the BMS 405 may determine a degradation state or a remaining lifetime of the battery 320 by using the calculated internal resistance value of the battery 320.

Figure 8:
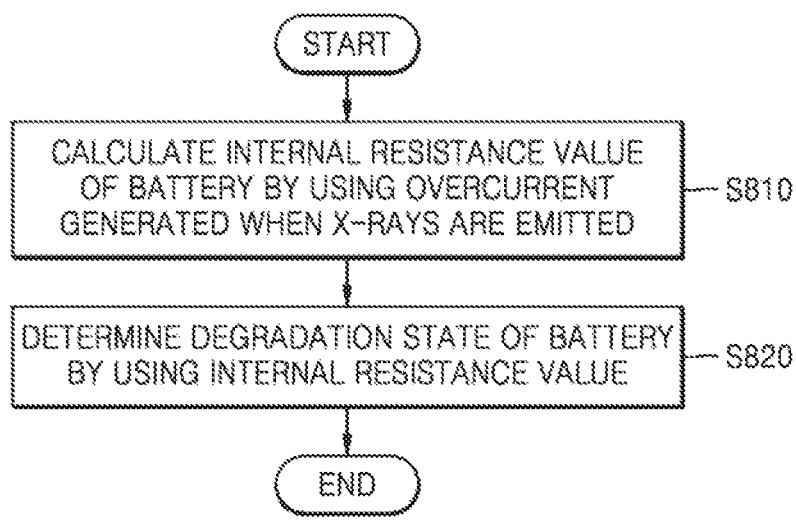
FIG. 8 is a flowchart of a method of operating the X-ray apparatus, according to an example embodiment.

FIG. 8 is a flowchart of a method of operating the X-ray apparatus 100 according to an example embodiment.

The method of FIG. 8 may be performed by elements of the X-ray apparatus 100 of any of FIGS. 1, 3, 4, and 7, and a repeated explanation will not be given.

In operation S810, the X-ray apparatus 100 may calculate an internal resistance value of a battery by using an overcurrent generated when X-rays are emitted. When the X-rays are emitted, overcurrent may temporarily flow through the battery and a voltage of the battery may be reduced due to the overcurrent. Accordingly, the X-ray apparatus 100 may calculate an internal resistance value of the battery based on a change in current and a voltage of the battery when the X-rays are emitted. According to an aspect of an example embodiment, the X-ray apparatus 100 may obtain an initial voltage value of the battery before the X-rays are emitted, may obtain a maximum current value and a minimum voltage value of the battery when the X-rays are emitted, and may calculate an internal resistance value of the battery by using the obtained initial voltage value, maximum current value, and minimum voltage value.

In operation S820, the X-ray apparatus 100 may determine a degradation state of the battery by using the internal resistance value calculated in operation S810. The X-ray apparatus 100 may determine a degradation state of the battery by comparing the initial internal resistance value of the battery with the calculated internal resistance value of the battery. Since an internal resistance increases as the battery is degraded, the X-ray apparatus 100 may determine how much the battery is degraded when compared to its initial state by checking how much the internal resistance value of the battery has increased from the initial internal resistance value.

Figure 9:
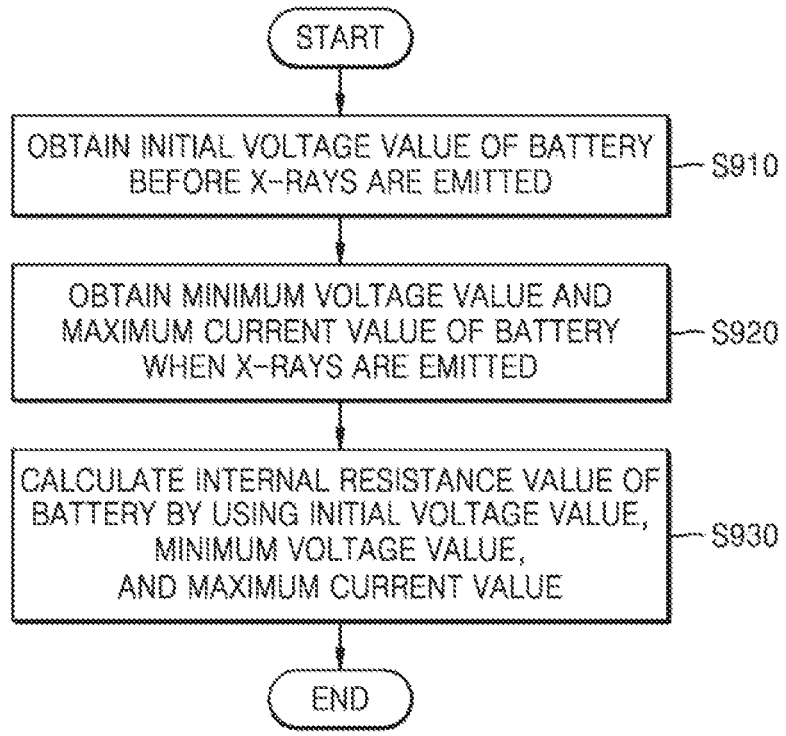
FIG. 9 is a flowchart of a method by which the X-ray apparatus calculates an internal resistance value of a battery.

FIG. 9 is a flowchart of a method by which the X-ray apparatus 100 calculates an internal resistance value of a battery.

In operation S910, the X-ray apparatus 100 may obtain an initial voltage value of a battery before X-rays are emitted. In more detail, the X-ray apparatus 100 may obtain an X-ray emission ready signal based on an X-ray emission command of a user. Next, the X-ray apparatus 100 may determine a voltage value of the battery corresponding to a point of time when the X-ray emission ready signal is generated as the initial voltage value.

In operation S920, the X-ray apparatus 100 may obtain a minimum voltage value and a maximum current value of the battery when the X-rays are emitted. The X-ray apparatus 100 may determine the maximum current value and the minimum voltage value of the battery when the X-rays are emitted, from among current values and voltage values obtained during a predetermined period from the point of time when the X-ray emission ready signal is generated to a predetermined time. In more detail, the X-ray apparatus 100 may determine a maximum value from among the current values of the battery obtained during the predetermined period as the maximum current value and may determine a minimum value from among the voltage values of the battery obtained during the predetermined period as the minimum voltage value.

In operation S930, the X-ray apparatus 100 may calculate an internal resistance value of the battery by using the initial voltage value, the minimum voltage value, and the maximum current value obtained in operations S910 and S920. For example, the X-ray apparatus 100 may calculate an internal resistance value of the battery by using Equation 1.

Figures 10, 11:
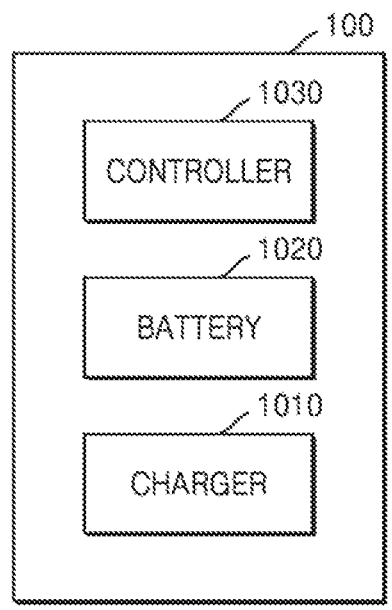
FIG. 10 is a block diagram of the X-ray apparatus according to another example embodiment.
FIG. 11 is a table illustrating an example where the controller measures a charging time of a battery by adjusting an operation mode, according to an example embodiment.

FIG. 10 is a block diagram of the X-ray apparatus 100 according to another example embodiment.

The X-ray apparatus 100 may include a battery 1020, a charger 1010, and a controller 1030. The X-ray apparatus 100 of FIG. 10 may be a mobile X-ray apparatus, like in FIG. 1, and only elements specifically related to the present embodiment are illustrated. Accordingly, it will be understood by one of ordinary skill in the art that elements other than the elements illustrated in FIG. 10 may be further included, such as one or more elements of FIG. 1.

The controller 1030 may correspond to the controller 120 of FIG. 1, and thus a repeated explanation will not be given. Also, the battery 1020 may correspond to the battery 320 of FIG. 3, and thus a repeated explanation will not be given.

The charger 1010 may charge the battery 1020. In more detail, the charger 1010 may supply charging power to charge the battery 1020. In this case, the charging power may refer to power generated by the charger 1010. According to an example embodiment, the charger 1010 may be coupled to an external power supply and may receive power from the external power supply. Next, the charger 1010 may supply the charging power to the battery 1020 by controlling the received power according to a user input or a calculation result of an internal device.

The controller 1030 may measure a charging time taken for the charger 1010 to charge the battery 1020, and may determine a degradation state of the battery 1020 by using the measured charging time. According to an example embodiment, the controller 1030 may determine a degradation state of the battery 1020 by comparing the measured charging time (e.g., from empty charge to full charge) of the battery 1020 with an initial charging time. Since a capacity of the battery 1020 is gradually reduced as the battery 1020 is degraded, the controller 1030 may determine how much the battery 1020 is degraded by checking how much the measured charging time of the battery 1020 is reduced from the initial charging time. For example, when the battery 1020 is completely degraded, a capacity of the battery 1020 may be half of an initial capacity, and the controller 1030 may determine a degradation state of the battery 1020 by checking how much the charging time taken for the charger 1010 to charge the battery 1020 is reduced from the initial charging time, which is a measured charging time when the battery 1020 is at its initial charging capacity with no degradation.

Also, according to another example embodiment, the controller 1030 may determine a degradation state of the battery 1020 by measuring a time during which current is discharged from the battery 1020. In a state where current is constantly discharged from the battery 1020, the controller 1030 may determine a degradation state of the battery 1020 by measuring a time during which the current is discharged from the battery 1020.

The controller 1030 may determine a degradation state of the battery 1020 by measuring a charging time taken for the charger 1010 to charge the battery 1020 in a state where the current discharged from the battery 1020 is controlled to be reduced. According to an example embodiment, the controller 1030 may determine a degradation state of the battery 1020 by measuring a charging time of the battery 1020 in a state where the current discharged from the battery 1020 to the controller 1030 is controlled at a reduced discharge rate (e.g., a state of reduced rate of discharge).

The controller 1030 may adjust an operation mode of the controller 1030 in order to control the current discharged from the battery 1020 to the controller 1030 to be reduced. According to an example embodiment, the controller 1030 may operate in a sleep mode that is a power saving state in order to control current discharged from the battery 1020 to the controller 1030 to be reduced. Accordingly, the controller 1030 may determine a degradation state of the battery 1020 by measuring a charging time taken for the charger 1010 to charge the battery 1020 in a sleep mode. According to another example embodiment, the controller 1030 may operate in a power-off mode in which only a minimum function (e.g., monitoring a battery charging status) is performed, in order to control current discharged from the battery 1020 to the controller 1030 to be reduced. For example, for a power-off mode, the controller 1030 may operate only a module that operates with regular power and may cut off power supply to other modules. Accordingly, the controller 1030 may determine a degradation state of the battery 1020 by measuring a charging time taken for the charger 1010 to charge the battery 1020 through the module that operates with regular power in the power-off mode.

Also, the controller 1030 may measure a charging time taken for the charger 1010 to charge the battery 1020 and may determine a remaining lifetime of the battery 1020 by using the measured charging time (e.g., from empty charge to full charge). The controller 1030 may determine a remaining lifetime of the battery 1020 by checking how much the measured charging time of the battery 1020 is reduced from an initial charging time. For example, assuming that a charging time of the battery 1020 is half of an initial charging time when the battery 1020 is completely degraded and a total lifetime of the battery is 4 years, the controller 1030 may detect that a charging time of the battery 1020 is ¾ times the initial charging time and may determine that a remaining lifetime of the battery 1020 is approximately 2 years.

The controller 1030 may measure a charging time taken for the charger 1010 to charge the battery 1020 according to each operation mode. According to an example embodiment, the controller 1030 may measure a charging time taken for the charger 1010 to charge the battery 1020 in a driving mode (e.g., normal operation mode) in which the X-ray apparatus 100 is driven. According to another example embodiment, the controller 1030 may measure a charging time taken for the charger 1010 to charge the battery 1020 in a sleep mode that is a power saving state. According to another example embodiment, the controller 1030 may measure a charging time taken for the charger 1010 to charge the battery 1020 in a power-off mode in which only a minimum operation is performed. Accordingly, the controller 1030 may determine a degradation state of the battery 1020 based on a charging time of the battery 1020 measured according to each operation mode.

In order to measure a charging time taken for the charger 1010 to charge the battery 1020, the controller 1030 may check a first point of time when a voltage of the battery 1020 reaches a first value and a second point of time when a voltage of the battery 1020 reaches a second value, and may determine a time between the first point of time and the second point of time as a charging time taken for the charger 1010 to charge the battery 1020. For example, the controller 1030 may activate a timer at a point of time when a voltage of the battery 1020 reaches the first value and may deactivate the timer at a point of time when a voltage of the battery 1020 reaches the second value. Accordingly, the controller 1030 may measure a charging time of the battery 1020 by using an operation time of the timer. Also, the controller 1030 may measure a charging time taken for the charger 1010 to charge the battery 1020 in a state where the charger 1010 charges the battery 1020 with a constant charging current.

Accordingly, since the X-ray apparatus 100 that is a mobile X-ray apparatus measures a charging time taken for the charger 1010 to charge the battery 1020 in a state where a current discharged from the battery 1020 is controlled at a reduced discharge rate, the X-ray apparatus 100 may more reliability measure the charging time. In the related art, since a current discharged to a controller that is a load even while a battery is charged is not constant, a deviation of a charging time of the battery may be large. However, in the present disclosure, since a charging time taken for the charger 1010 to charge the battery 1020 is measured in a state where current discharged from the battery 1020 to the controller 1020 is controlled at a reduced discharge rate, the charging time may be more reliably measured.

FIG. 11 is a table 1100 illustrating an example where the controller 1030 measures a charging time of the battery 1020 by adjusting an operation mode according to an example embodiment.

When the charger 1010 charges the battery 1020, the controller 1030 may measure a charging time of the battery 1020 in a state where an operation mode is adjusted. According to an example embodiment, the controller 1030 may measure a charging time of the battery 1020 in a driving mode for driving the X-ray apparatus 100 that is a mobile X-ray apparatus. According to another example embodiment, the controller 1030 may measure a charging time of the battery 1020 in a sleep mode that is a power saving state. According to another example embodiment, the controller 1030 may measure a charging time of the battery 1020 in a power-off mode in which only a minimum function is performed. Accordingly, since the controller 1030 may measure a charging time of the battery 1020 in a driving mode, a sleep mode, or a power-off mode for reducing current discharged from the battery 1020, the charging time may be more reliably measured.

The controller 1030 may manage the table 1100 showing information about a charging time of the battery 1020 according to each operation mode, and may determine a degradation state of the battery 1020 based on the table 1100.

For example, when a charging time of the battery 1020 measured in a power-off mode is 1.5 hours, since 1.5 hours that is a current charging time is an intermediate value (e.g., half-way point) between 2 hours that is an initial charging time and 1 hour that is a charging time after full degradation, the controller 1030 may determine that the battery 1020 is degraded by about 50%. Thus, the degradation state of the battery 1020 may be represented by the formula, (current charging time−charging time after full degradation)/(initial charging time−charging time after full degradation)×100%. Alternatively, the relationship between the charging time and the degradation state may be a non-linear relationship. Also, the controller 1030 may determine about N/2 years of a total lifetime of N years as a remaining lifetime of the battery 1020.

Also, the controller 1030 may determine a remaining lifetime of the battery 1020 as N2, based on the degradation state of the battery 1020 and a total lifetime of N years.

According to an example embodiment, the controller 1030 may measure charging times of the battery 1020 in a driving mode, a sleep mode, and a power-off mode and may compare the charging times, in order to more reliably determine a degradation state of the battery 1020.

FIG. 12 is a flowchart of a method of operating the X-ray apparatus 100 according to an example embodiment.

The method of FIG. 12 may be performed by elements of the X-ray apparatus 100 of any of FIGS. 1 and 11, and a repeated explanation will not be given.

In operation S1210, the X-ray apparatus 100 may determine whether a battery is being charged. For example, when a power plug of the X-ray apparatus 10 is connected to an external power socket, the X-ray apparatus 100 may determine that the battery is being charged.

When it is determined in operation S1210 that the battery is being charged, the method proceeds to operation S1220. In operation S1220, the X-ray apparatus 100 may control a discharge rate of a current discharged from the battery at a reduced rate. According to an example embodiment, the X-ray apparatus 100 may control current discharged from the battery to a controller to be reduced. According to an example embodiment, the X-ray apparatus 100 may operate in a sleep mode in which a controller is in a power saving state, in order to keep the discharge rate of the current discharged from the battery at a reduced rate. According to another example embodiment, the X-ray apparatus 100 may operate in a power-off mode in which the controller performs only a minimum function, in order to control current discharged from the battery to the controller to be reduced. For example, for the power-off mode, the X-ray apparatus 100 may maintain power supply to only a function for measuring a charging time of the battery and may cut off power supply to other functions of the controller. Accordingly, the X-ray apparatus 100 may perform operations S1240 through S1260 in a state where current discharged from the battery is controlled to be reduced.

In operation S1230, the X-ray apparatus 100 may determine whether a voltage of the battery reaches a first value. A voltage of the battery that is being charged may gradually increase. Accordingly, the X-ray apparatus 100 may determine whether a voltage of the battery reaches the first value. For example, the X-ray apparatus 100 may determine whether a voltage of the battery reaches 340V.

When it is determined in operation S1230 that a voltage of the battery reaches the first value, the method may proceed to operation S1240. In operation S1240, the X-ray apparatus 100 may start to measure a charging time of the battery. According to an example embodiment, when a voltage of the battery reaches the first value, the X-ray apparatus 100 may activate a timer.

In operation S1250, the X-ray apparatus 100 may determine whether a voltage of the battery reaches a second value. In other words, the X-ray apparatus 100 may determine whether a voltage of the battery reaches the second value after the first value. For example, the X-ray apparatus 100 may determine whether a voltage of the battery reaches 356V.

When it is determined in operation S1250 that a voltage of the battery reaches the second value, the method proceeds to operation S1260. In operation S1260, the X-ray apparatus 100 may stop measuring the charging time of the battery. According to an example embodiment, when a voltage of the battery reaches the second value, the X-ray apparatus 100 may deactivate the timer that is activated in operation S1240.

In operation S1270, the X-ray apparatus 100 may determine a degradation state of the battery by using the charging time of the battery measured in operations S1240 through S1260. For example, the X-ray apparatus 100 may determine a degradation state of the battery by using an operation time of the timer.

The device described herein may include a processor, a memory for storing and executing program data, a permanent storage unit such as a disk drive, a communications port for handling communications with external devices, and user interface devices, including a touch panel, keys, buttons, etc. When software modules or algorithms are involved, these software modules may be stored as program instructions or computer-readable codes executable on a processor on a computer-readable medium. Examples of the computer-readable recording medium include magnetic storage media (e.g., read-only memories (ROMs), random-access memories (RAMs), floppy disks, hard disks, etc.), and optical recording media (e.g., compact disc (CD)-ROMs, or digital versatile discs (DVDs)). The computer-readable recording medium may also be distributed over network coupled computer systems so that the computer-readable code is stored and executed in a distributive manner. This medium may be read by the computer, stored in the memory, and executed by the processor.

The present disclosure may be described in terms of functional block components and various processing steps. Such functional blocks may be realized by any number of hardware and/or software components configured to perform the specified functions. For example, the present disclosure may employ various integrated circuit (IC) components, e.g., memory elements, processing elements, logic elements, look-up tables, and the like, which may carry out a variety of functions under the control of one or more microprocessors or other control devices. Similarly, where the elements of the present disclosure are implemented using software programming or software elements, the disclosure may be implemented with any programming or scripting language such as C, C++, Java, assembler language, or the like, with the various algorithms being implemented with any combination of data structures, objects, processes, routines or other programming elements. Functional aspects may be implemented in algorithms that are executed on one or more processors. Furthermore, the present disclosure could employ any number of conventional techniques for electronics configuration, signal processing and/or control, data processing and the like. The words "mechanism," "element," "means," and "configuration" are used broadly and are not limited to mechanical or physical embodiments, but may include software routines in conjunction with processors, etc.

What is claimed is:

1. A mobile X-ray apparatus comprising:
   an X-ray emitter;
   a battery configured to supply operating power to the X-ray emitter;
   a battery management system (BMS) configured to detect a state of the battery including a voltage of the battery; and
   a controller configured to:
   in response to X-rays being emitted, obtain information about a voltage value of the battery detected by the BMS,
   calculate an internal resistance value of the battery based on the information, and
   determine a degradation state of the battery by using the calculated internal resistance value.

2. The mobile X-ray apparatus of claim 1, wherein the controller is further configured to:
   obtain an initial voltage value of the battery before the X-rays are emitted,
   obtain a maximum current value of the battery and a minimum voltage value of the battery when the X-rays are emitted, and
   calculate the internal resistance value based on the minimum voltage value and the maximum current value.

3. The mobile X-ray apparatus of claim 2, wherein the controller is further configured to:
   determine the initial voltage value of the battery at a point of time when an X-ray emission ready signal is generated,
   determine the maximum current value from among current values of the battery obtained during a predetermined period from the point of time to a predetermined time, and
   determine the minimum voltage value from among voltage values of the battery obtained during the predetermined period.

4. The mobile X-ray apparatus of claim 2, further comprising:
a user interface configured to receive a user input of a user of the mobile X-ray apparatus,
wherein the controller is further configured to:
receive an X-ray emission ready signal based on the user input;
obtain the initial voltage value of the battery based on the received X-ray emission ready signal.

5. The mobile X-ray apparatus of claim 1, wherein the battery management system (BMS) is further configured to detect a current value of the battery,
wherein the controller is further configured to periodically obtain the voltage value and the current value of the battery from the BMS.

6. The mobile X-ray apparatus of claim 1, further comprising a display,
wherein the controller is further configured to determine a remaining lifetime of the battery based on the internal resistance value of the battery, and
wherein the display is configured to display the determined remaining lifetime of the battery.

7. The mobile X-ray apparatus of claim 1, wherein the controller is further configured to determine the degradation state of the battery by comparing an initial internal resistance value of the battery with the calculated internal resistance value.

8. The mobile X-ray apparatus of claim 1,
wherein the BMS is further configured to calculate the internal resistance value of the battery based on a current value of the battery generated when the X-rays are emitted by the X-ray emitter and transmit the calculated internal resistance value to the controller, and
wherein the controller is further configured to determine the degradation state of the battery based on the transmitted internal resistance value.

9. The mobile X-ray apparatus of claim 1, wherein the battery is a lithium-ion battery.

10. A method of operating a mobile X-ray apparatus comprising a battery, the method comprising:
detecting a state of the battery including a voltage of the battery;
in response to X-rays being emitted, obtain information about a voltage value;
calculating an internal resistance value of the battery based on the information; and
determining a degradation state of the battery by using the calculated internal resistance value.

11. The method of claim 10, wherein the obtaining information comprise:
obtaining an initial voltage value of the battery before the X-rays are emitted;
obtaining a maximum current value of the battery and a minimum voltage value of the battery when the X-rays are emitted; and
calculating the internal resistance value based on the initial voltage value, the minimum voltage value, and the maximum current value.

12. The method of claim 11, wherein the obtaining the initial voltage value comprises determining the initial voltage value of the battery at a point of time when an X-ray emission ready signal is generated,
wherein the obtaining the maximum current value and the minimum voltage value comprises determining the maximum current value from among current values of the battery obtained during a predetermined period from the point of time to a predetermined time, and determining the minimum voltage value from among voltage values of the battery obtained during the predetermined period.

13. The method of claim 10, further comprising:
determining a remaining lifetime of the battery based on the internal resistance value of the battery; and
displaying the determined remaining lifetime of the battery.

14. The method of claim 10, wherein the determining the degradation state of the battery comprises comparing an initial internal resistance value of the battery with the calculated internal resistance value.

15. The method of claim 10, wherein the battery is a lithium-ion battery.

16. A computer-readable recording medium having embodied thereon a program for executing the method of claim 10 in a computer.

17. A mobile X-ray apparatus comprising:
an X-ray emitter;
a battery configured to supply operating power to the X-ray emitter;
a battery management system (BMS) configured to detect a state of the battery including a current of the battery; and
a controller configured to:
in response to X-rays being emitted, obtain information about a current value of the battery detected by the BMS;
calculate an internal resistance value of the battery based on the information; and
determine a degradation state of the battery by using the calculated internal resistance value.

* * * * *